(12) United States Patent
Szesni et al.

(10) Patent No.: US 9,327,272 B2
(45) Date of Patent: May 3, 2016

(54) METHOD FOR PRODUCING A COMPOSITE MATERIAL

(75) Inventors: Normen Szesni, Rosenheim (DE); Melanie Kaiser, Grosskarolinenfeld (DE); Richard Fischer, Bad Aibling (DE); Hans-Jörg Wölk, Rosenheim (DE)

(73) Assignee: Clariant International Ltd., Muttenz (CH)

( * ) Notice: Subject to any disclaimer, the term of this patent is extended or adjusted under 35 U.S.C. 154(b) by 123 days.

(21) Appl. No.: 13/504,276

(22) PCT Filed: Oct. 27, 2010

(86) PCT No.: PCT/EP2010/006561
§ 371 (c)(1),
(2), (4) Date: Oct. 15, 2012

(87) PCT Pub. No.: WO2011/050953
PCT Pub. Date: May 5, 2011

(65) Prior Publication Data
US 2013/0041193 A1    Feb. 14, 2013

(30) Foreign Application Priority Data
Oct. 30, 2009 (DE) .......................... 10 2009 051 462

(51) Int. Cl.
*B01J 37/02* (2006.01)
*C07C 5/05* (2006.01)
(Continued)

(52) U.S. Cl.
CPC ............ *B01J 23/462* (2013.01); *B01J 31/0284* (2013.01); *B01J 31/0292* (2013.01); *B01J 31/0294* (2013.01); *B01J 31/20* (2013.01); *B01J 35/002* (2013.01); *B01J 35/008* (2013.01); *B01J 35/0086* (2013.01); *B01J 35/0093* (2013.01); *B01J 37/0203* (2013.01); *B01J 37/0205* (2013.01); *C07C 5/05* (2013.01); *C07C 5/09* (2013.01); *B01J 21/08* (2013.01); *B01J 31/0288* (2013.01); *B01J 37/0219* (2013.01); *B01J 37/0223* (2013.01); *B01J 37/0232* (2013.01); *B01J 37/0248* (2013.01); *B01J 37/08* (2013.01); *B01J 2231/645* (2013.01); *B01J 2531/821* (2013.01)

(58) Field of Classification Search
None
See application file for complete search history.

(56) References Cited

U.S. PATENT DOCUMENTS 4,404,124 A    9/1983   Johnson
4,409,410 A   10/1983   Cosyns et al.
(Continued)

FOREIGN PATENT DOCUMENTS

CN    1538876 A    10/2004
CN  101045213 A    10/2007
(Continued)

OTHER PUBLICATIONS

Manual of Methods and Procedures for Catalyst Characterization J. Haber, J.H. Block, B. Delmon Pure and Applied Chemistry vol. 67, No. 8/9, pp. 1257-1306 1995.*
(Continued)

*Primary Examiner* — Melvin C Mayes
*Assistant Examiner* — Douglas Call
(74) *Attorney, Agent, or Firm* — Anthony A. Bisulca

(57) ABSTRACT

A method for producing a composite material which contains a support material and an ionic liquid, as well as a composite material and its use as synthetic catalyst.

11 Claims, 5 Drawing Sheets

(51) Int. Cl.

| | | |
|---|---|---|
| *B01J 35/02* | (2006.01) | |
| *B01J 23/46* | (2006.01) | |
| *B01J 31/02* | (2006.01) | |
| *B01J 31/20* | (2006.01) | |
| *B01J 35/00* | (2006.01) | |
| *C07C 5/09* | (2006.01) | |
| *B01J 21/08* | (2006.01) | |
| *B01J 37/08* | (2006.01) | |

(56) References Cited

U.S. PATENT DOCUMENTS

| | | | |
|---|---|---|---|
| 4,837,189 A | 6/1989 | Simon et al. | |
| 4,977,126 A * | 12/1990 | Mauldin et al. | 502/242 |
| 5,089,245 A | 2/1992 | Eyman et al. | |
| 5,648,576 A | 7/1997 | Nguyen Than et al. | |
| 5,672,734 A * | 9/1997 | Abel et al. | 560/245 |
| 5,693,585 A | 12/1997 | Benazzi et al. | |
| 6,040,263 A | 3/2000 | Mussmann et al. | |
| 6,465,391 B1 | 10/2002 | Cheung | |
| 6,603,038 B1 | 8/2003 | Hagemeyer et al. | |
| 6,969,693 B2 | 11/2005 | Sauvage et al. | |
| 7,026,266 B2 * | 4/2006 | Chaudhari | B01J 27/188 502/155 |
| 7,381,845 B2 | 6/2008 | Weiskopf et al. | |
| 7,799,373 B2 | 9/2010 | Sachweh et al. | |
| 7,799,730 B2 | 9/2010 | Ringer et al. | |
| 8,334,232 B2 | 12/2012 | Jess | |
| 2002/0198100 A1 | 12/2002 | Mehnert et al. | |
| 2004/0059153 A1 | 3/2004 | Magna et al. | |
| 2004/0235650 A1 | 11/2004 | Saleh et al. | |
| 2005/0033102 A1 | 2/2005 | Randolph et al. | |
| 2005/0181940 A1 | 8/2005 | Wang et al. | |
| 2006/0217579 A1 | 9/2006 | Bailey | |
| 2008/0269533 A1 | 10/2008 | Chang et al. | |
| 2009/0026691 A1 | 1/2009 | Ishikawa | |
| 2009/0256113 A1 | 10/2009 | Borchers | |
| 2009/0264691 A1 | 10/2009 | Jess et al. | |
| 2010/0190638 A1 | 7/2010 | Hagemeyer et al. | |
| 2010/0197488 A1 | 8/2010 | Hagemeyer et al. | |
| 2010/0217052 A1 | 8/2010 | Ungar et al. | |
| 2010/0273644 A1 | 10/2010 | Hagemeyer et al. | |
| 2011/0166010 A1 | 7/2011 | Hagemeyer et al. | |
| 2013/0041193 A1 | 2/2013 | Szesni | |

FOREIGN PATENT DOCUMENTS

| | | |
|---|---|---|
| DE | 31 19 850 A1 | 2/1982 |
| DE | 197 34 974 A1 | 2/1999 |
| DE | 103 15 215 A1 | 10/2004 |
| DE | 10 2006 019 460 A1 | 10/2007 |
| DE | 10-2007 025 317 A1 | 12/2008 |
| DE | 10 2007 025 362 A1 | 12/2008 |
| DE | 10 2007 025 443 A1 | 12/2008 |
| EP | 0 064 301 A1 | 11/1982 |
| EP | 0 553 815 A1 | 8/1993 |
| EP | 0 780 155 A1 | 6/1997 |
| EP | 1 120 159 A1 | 8/2001 |
| EP | 1 364 936 A1 | 11/2003 |
| FR | 2 628 014 | 9/1989 |
| JP | 2009-502458 A | 1/2009 |
| JP | 2009502458 | 1/2009 |
| WO | WO 98/14274 | 4/1998 |
| WO | WO 99/03163 | 1/1999 |
| WO | WO 00/29108 | 5/2000 |
| WO | WO 01/32308 A1 | 5/2001 |
| WO | WO 02/078842 A1 | 10/2002 |
| WO | WO 02/094740 A2 | 11/2002 |
| WO | WO 02/096557 A1 | 12/2002 |
| WO | WO 02/098560 A1 | 12/2002 |
| WO | WO 2005/016855 A2 | 2/2005 |
| WO | WO 2005/123253 A1 | 12/2005 |
| WO | WO 2006/114320 A1 | 11/2006 |
| WO | WO 2006/122563 A1 | 11/2006 |
| WO | WO 2008/145387 A2 | 12/2008 |
| WO | WO 2008/145388 A1 | 12/2008 |
| WO | WO 2008/145391 A2 | 12/2008 |
| WO | WO 2011/029691 A1 | 3/2011 |
| WO | 2011050953 | 5/2011 |

OTHER PUBLICATIONS

Selective Catalytic Hydrodimerization of 1,3-Butadiene by Palladium Compounds Dissolved in Ionic Liquids Jeanne E. L. Dullius et al. Organometallics, vol. 17, pp. 815-819, 1998.*
Arras et al., *Regioselective catalytic hydrogenation of citral with ionic liquids as reaction modifiers*, Green Chem., 11:716-723 (2009).
Gu et al., *Ionic Liquids-Based Catalysis with Solids: State of the Art*, Adv. Synth. Catal., 351:817-847 (2009).
Huang et al., *Pd Nanoparticles Immobilized on Molecular Sieves by Ionic Liquids: Heterogeneous Catalysts for Solvent-Free Hydrogenation*, Angewandte Chem. Int. Ed., 43:1397-1399 (2004).
Mehnert et al., *Supported ionic liquid catalysis investigated for hydrogenation reactions*, The Royal Society of Chemistry pp. 3010-3011 (2002).
Mehnert et al., *Supported Ionic Liquid Catalysis—A New Concept for Homogeneous Hydroformylation Catalysis*, J. Am. Chem. Soc., 124:12932-12933 (2002).
Kernchen et al., *Solid Catalyst with Ionic Liquid Layer (SCILL)—A New Concept to Improve Selectivity Illustrated by Hydrogenation of Cyclooctadiene*, Chem. Eng. Technol., 30:985-994 (2007).
Virtanen et al., *Towards one-pot synthesis of menthols from citral: Modifying Supported Ionic Liquid Catalysts (SILCAs) with Lewis and Bronsted Acids*, Journal of Catalysis, 263:209-219 (2009).
International Search Report PCT/EP2010/006561 dated Nov. 17, 2011.
U.S. Appl. No. 13/276,403 (unpublished).
Joni, J., Development of a Supported Ionic Liquid Phase (SILP) Catalyst for Slurry-Phase Friedel-Crafts Alkylations of Cumene, Advanced Synthesis and Catalysis 2009, 351, 423-431.
Baudoux, J., Development of new SILP catalysts using chitosan as support, Green Chemistry 2007, 9, 1346-1351.
Riisager, R., Supported ionic liquids: versatile reaction and separation media, Topics in Catalysis 2006, 40, 91-101.
Mikkola, J.-P., Effect of Internal Diffusion in Supported Ionic Liquid Catalysts: Interaction with Kinetics, Industrial & Engineering Chemistry Research, 2007, 46, 3932-3940.
Hagiwara, H., Supported ionic liquid catalyst (Pd-SILC) for highly efficient and recyclable Suzuki-Miyaura reaction, Chemical Communications 2007, 2838-2840.
Wasserscheid, P., Ionische Flüssigkeiten-neue Lösungen für die Übergangsmetallkatalyse, Angewandte Chemie 2000, 112, 3926-3945.
Eigenberger, G., Fixed-Bed Reactors, Ullmann's Encyclopedia, 6th Edition, 2000, Electronic Release, Chapter Fixed-Bed Reactors, Par. 2: Catalyst for fixed-bed reactors.
Arras et al., *The promoting effect of a dicyanamide based ionic liquid in the selective hydrogenation of citral*, Chem. Commun., 4058-4060 (2008).
Breitenlechner et al., *Solid Catalysts on the Basis of Supported Ionic Liquids and Their Use in Hydroamination Reactions*; Journal of Molecular Catalysis A: Chemical 214:175-179 (2004).
Decastro et al., *Immobilised Ionic Liquids as Lewis Acid Catalysts for the Alkylation of Aromatic Compounds with Dodecene*, Journal of Catalysis, 196:86-94 (2000).
Gallezot, Fundamental Aspects of Heterogeneous Catalytic Hydrogenation, Encyclopedia of Catalysis, John Wiley & Sons, available on-line Jul. 15, 2002.
Huang, et al., *Pd Nanoparticles Immobilized on Molecular Sieves by Ionic Liquids: Heterogeneous Catalysts for Solvent-Free Hydrogenation*, Angewandte Chemie, 43:1397-1399 (2004).
Leofanti et al., *Surface Area and Pore Texture of Catalysts*, Catalysis Today, 41:207-219 (1998).
Mehnert, *Supported Ionic Liquid Catalysis*, Chemistry European Journal, 11:50-56 (2005).

(56) References Cited

OTHER PUBLICATIONS

Mikkola et al., *Supported Ionic Liquids Catalysts for Fine Chemicals: Citral Hydrogenation*, The Royal Society of Chemistry, 8: 197-205 (2006).

Ruta et al., *Pd Nanoparticles in a Supported Ionic Liquid Phase: Highly Stable Catalysts for Selective Acetylene Hydrogenation under Continuous-Flow Conditions*, J. Phys. Chem, 112:17814-17819 (2008).

Zeolyst product list as of Mar. 24, 2005, available through Internet Archive.org.

Arras, Jurgen, "Einfluss ionisccher Flussigkeiten mit funktionalisierten Kationen auf . . . " Chemie Ingenieur Technik, (2009), 81, No. 12, pp. 2007-2011.

Arras, Jurgen, "How a Supported Metal is Influenced by an Ionic Liquid: In-Depth Characterization . . . " J. Phys. Chem. C (2010), 114, pp. 10520-10526.

Arras, Jurgen, "Supported ruthenium catalysed selective hydrogeneration of citral . . . " Applied Catalysis A: General (2009), 371, pp. 73-77.

Hermann, Tanja, "High-Performance Supported Catalysts with an Ionic Liquid . . . " Chem. Commun., (2011), 47, pp. 12310-12312.

Kiwi-Minsker, Lioubov, "Structured Catalytic Wall Microreactor for Efficient Performance of Exothermic Reactions," Chemical Engineering and Processing 49, pp. 973-978 (2010).

Ranting Tao, et al., "Pd nanoparticles immobilized on sepiolite by ionic liquids: efficient catalysts for hydrogenation of alkenes and Heck reactions," Green Chemistry 11(1), 96-101, Jan. 2009.

Schwab, Frederick, "Ruthenium-catalyzed selective hydrogenation of Benzene to . . . " Angew. Chem. Int. Ed. (2011), 50, pp. 10453-10456.

Sobota, Marek, "Ligand Effects in SCILL Model Systems: Site-Specific . . . " Adv. Mater. (2011), 23, pp. 2617-2621.

Steinrueck, H.P., "Surface Science and Model Catalysis with Ionic . . . " Adv. Mater. (2011), 23, pp. 2571-2587.

Wasserscheid, Peter, "Ionic Liquids—New Soluations for Transition Metal Catalysis" Angew. Chem. Int. Ed. (2000), 39, pp. 3772-3789.

\* cited by examiner

METHOD FOR PRODUCING A COMPOSITE MATERIAL

CROSS-REFERENCE TO RELATED APPLICATIONS

This application is a U.S. National Stage application claiming benefit of International Application No. PCT/EP2010/006561, filed Oct. 27, 2010, and claiming benefit of German Application No. DE 10 2009 051 462.7, filed Oct. 30, 2009. The entire disclosures of both PCT/EP2010/006561 and DE 10 2009 051 462.7 are incorporated herein by reference.

BACKGROUND

The present invention relates to a method for producing a composite material which contains a support material and an ionic liquid, as well as a composite material and its use as synthetic catalyst.

Materials that consist of a solid support component and a liquid component immobilized thereon have been examined intensively in the more recent past. The supporting of the liquid component and substances possibly dissolved or suspended therein gives the composite excellent new properties. Above all, the immobilization of ionic liquids (IL) on porous support materials is the focus of the interest here. The resultant composites can be used in industrially important fields such as catalysis, gas cleaning, the purification of fuel mixtures, the separation of mixtures, rheology and many more.

In the field of catalysis, two thematically related concepts are studied above all:

In the case of the so-called SILP (Supported Ionic Liquid Phase) concept [J. Joni, M. Haumann, P. Wasserscheid, Advanced Synthesis and Catalysis 2009, 351, 423-431; J. Baudoux, K. Perrigaud, P.-J. Madec, A.-C. Gaumont, I. Dez, Green Chemistry 2007, 9, 1346-1351; A. Riisager, R. Fehrmann, M. Haumann, P. Wasserscheid, Topics in Catalysis 2006, 40, 91-101] (also called SILCA [P. Virtanen, H. Karhu, G. Toth, K. Kordas, J.-P. Mikkola, Journal of Catalysis 2009, 263, 209-219; J.-P. Mikkola, J. Wärna, P. Vitanen, T. Salmi, Industrial & Engineering Chemistry Research 2007, 46, 3932-3940] or SILC [H. Hagiwara, K.-H. Ko, T. Hoshi, T. Suzuki, Chemical Communications 2007, 2838-2840]), ionic catalyst solutions are immobilized on porous support materials. The ionic catalyst solution consists of at least one ionic liquid, as well as at least one further catalytically active component. The catalytically active component can be an organometallic complex compound, metal nanoparticle, an organic catalyst or also a biocatalyst such as e.g. an enzyme. In addition, the ionic liquid itself can also act as catalyst for a reaction or serve as co-catalyst for the dissolved or suspended catalyst.

In the case of the so-called SCILL (Solid Catalysts with Ionic Liquid Layer) concept, ionic liquids or compositions containing an ionic liquid are immobilized on a solid (preformed) catalyst. The properties of the heterogeneous catalyst change as a result. In some cases, a dramatically increased selectivity in favour of the desired product was able to be observed while activity remained constant [J. Arras, M. Steffan, Y. Shayeghi, D. Ruppert, P. Claus, Green Chemistry 2009, 11, 716-723; U. Kernchen, B. Etzold, W. Korth, A. Jess, Chemical Engineering & Technology 2007, 30, 985-994].

Both of the named concepts can be used in all known reactor designs, such as for example an aerated or unaerated suspension reactor, a bubble column reactor, a fluid-bed reactor or a fixed-bed reactor. The particular properties of ionic liquids, such as non-vaporability, make SILP and SCILL catalysts particularly suitable for continuous gas-phase processes in fixed-bed reactors.

As a rule, such catalyst compositions are produced according to the state of the art by wet-chemical impregnation. The ionic liquid and any further (catalytically active) components such as a homogeneous catalyst or metal nanoparticle are dissolved in a suitable solvent (or suspended or emulsified) and the support is then added.

In order to obtain a uniform coating of the support with the ionic catalyst solution, in the methods of the state of the art the quantity of solvent is greater than the pore volume of the support material used. The solvent of the resultant suspension is then removed slowly. An externally dry material with a visually uniform coating is thus obtained. The disadvantage of the method is above all the great length of time required. However, if the solvent vaporizes too quickly, the dissolved components precipitate prematurely and a poor coating results. The removal of the solvent has also been carried out by standing the suspension in air, by expulsion using a gas stream or by freeze-drying, but the length of time required is even greater in all these methods. The slow evaporation of the solvent is important however: because the quantity of solvent is greater than the pore volume of the support, not all of the ionic liquid used is located in the pores of the support. If evaporation is too fast, the ionic liquid precipitates in an uncontrolled manner and a uniform coating is not achieved. In order to achieve a uniform coating with this method, the length of time required is thus very great.

If the quantity of solvent is reduced, so that it is smaller than or equal to the pore volume of the support material, the term incipient wetness impregnation is used. The length of time required in this case is much less, but the coating is often non-homogeneous and not reproducible.

Thus, for example, WO 2006/122563 A1 discloses the production of an SILP catalyst in which a silicate support is stirred in a solution containing an ionic liquid, wherein the SILP catalyst is obtained after the solvent has been drawn off.

US 2005/0033102 likewise discloses the production of a supported ionic liquid, wherein a support is introduced into an ionic liquid.

In the same way as in WO 2006/122563 A1, WO 02/098560 discloses a method for producing a supported composition in which an ionic liquid is applied to a support by introducing a support into an ionic liquid dissolved in a solvent, followed by vaporization of the solvent. An immobilized ionic liquid is produced in the same way in WO 01/32308.

EP 1 364 936 B1 discloses the production of a supported ionic liquid by mixing an ionic liquid with a support.

In addition to the disadvantage of the great length of time required and the fact that the coating is often produced non-homogeneous and not reproducible, the methods according to the state of the art give satisfactory results only when pulverulent support materials are coated. In the case of shaped bodies such as tablets, spheres, cones, rings, strands, hollow strands, trilobes, solid cylinders, hollow cylinders or grit, a homogeneous distribution of the ionic catalyst solution on the support material cannot be readily achieved, i.e. the distribution of the ionic catalyst solution cannot be set specifically, and is random. This is to be attributed in particular to the properties of ionic liquids, such as for example strong surface tension and high viscosity compared with the solvent. The smaller the support particles to be coated are, the smaller the part played by aggregation effects due to van der Waals forces. In the case of powders, therefore, a homogeneous distribution of the coating can be achieved. In the case of more complex shaped bodies, however, the named properties of ionic liquids come to bear more strongly, with the result that a high uniformity of the coating cannot be achieved with the conventional methods.

SUMMARY

It was thus an object of the present invention to provide a method for producing composite materials consisting of a support material and an ionic liquid, which does not have disadvantages associated with the state of the art to the above-named extent, and in particular makes it possible to carry out the coating easily, which can also be applied to specific shaped bodies and allows the morphology of the composite material to be set in targeted manner.

In addition, it was an object of the present invention to develop a time-saving method for producing composite materials in which an extremely homogeneous coating with uniform shell thickness can be achieved not only in the case of pulverulent support bodies but also in the case of support bodies with more complex shapes.

These and other objects according to aspects of the invention is achieved by providing a method for producing a composite material containing a support material and an ionic liquid, wherein a solution, suspension or emulsion which contains the ionic liquid is applied by spray impregnation onto the support material fluidized in a fluidized bed.

DETAILED DESCRIPTION

Figure 1:
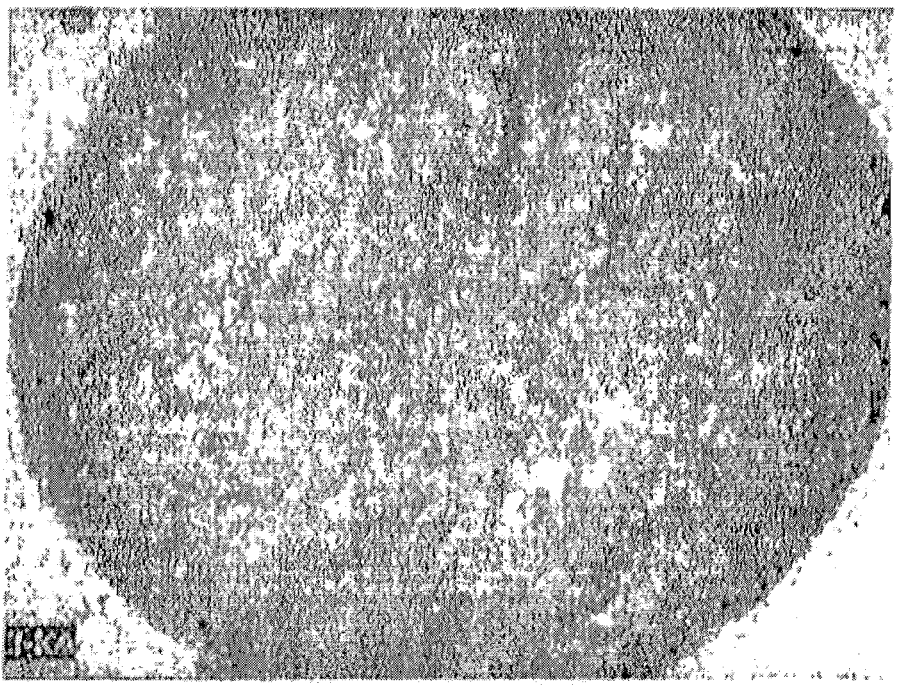
FIG. 1 is a scanning electron microscopy image of the distribution of the homogeneous catalyst of Example 1.

According to the definition offered by Wasserscheid and Keim in "Angewandte Chemie" 2000, 112, pages 3926 to 3945, ionic liquids are salts that melt at a relatively low temperature. Ionic liquids are therefore already liquid at relatively low temperatures. In addition, they are in general not combustible and have no measurable vapour pressure.

Within the framework of the present invention, by the term "ionic liquids" are meant salts which have a melting point or melting point range that lies below 200° C., preferably below 150° C. and particularly preferably below 100° C.

Furthermore, the ionic liquids are preferably those that have a molar mass of preferably at most 400 g/mol, particularly preferably at most 800 g/mol.

Furthermore, preferred ionic liquids are those with cations of organic nature and with anions of organic or inorganic nature. Ionic liquids are formed from positive and negative ions, but overall are neutral in charge. Both the positive and the negative ions are predominantly monovalent, but multivalent anions and/or cations which have up to 5, preferably up to 4, particularly preferably up to 3 and particularly preferably up to 2 electrical charges are also possible. The charges inside the respective ion can be either localized or delocalized.

The present invention is not limited to composite materials the internal surface of which is coated with a particular ionic liquid; all suitable ionic liquids can be used, also including mixtures of different ionic liquids.

The fluidized bed or fluid bed according to aspects of the present invention can be achieved by means of a fluidized bed unit or fluid bed unit. It is particularly preferred if the unit contains a so-called controlled air-glide layer. For one thing, the support material bodies are thoroughly mixed by the controlled air-glide layer, wherein at the same time they rotate about their own axis. They are uniformly dried by the process gas used for this. For another thing, the support material bodies pass through the spraying process at a virtually constant frequency because of the consistent orbital movement of the support material brought about by the controlled process gas-glide layer. The solution containing the ionic liquid can be applied using the top-spray, bottom-spray (Wurster) or tangential (rotor pellet) method. The presence of the support material in a fluidized bed or fluid bed in the named manner swirled in the latter by the process gas is also meant by the expression "fluidized in a fluidized bed or fluid bed".

A largely uniform shell thickness of a treated batch of shaped bodies is achieved because the support material is present fluidized in a fluidized bed or fluid bed. Furthermore, it is achieved through this that the concentration of the ionic liquid applied by the spraying process, or the further additives contained in the solution according to the invention, varies only relatively little over a relatively large area of the shell thickness, i.e. the concentration of the ionic liquid or the optional additives describes a roughly rectangular function over a large area of the shell thickness, whereby a largely uniform distribution on the support material shaped body is guaranteed. Suitable fluidized bed units or fluid bed units for carrying out the method according to aspects of the invention in accordance with preferred embodiments are known in the state of the art and are marketed e.g. by Heinrich Brucks GmbH (Alfeld, Germany) ERWEK GmbH (Heusenstamm, Germany), Stechel (Germany), DRIAM Anlagenbau GmbH (Eriskirch, Germany), Glatt GmbH (Binzen, Germany), G. S. Divisione Verniciatura (Osteria, Italy), HOFER-Pharma Maschinen GmbH (Weil am Rhein, Germany), L. B. Bohie Maschinen+Verfahren GmbH (Enningerloh, Germany), Lödige Maschinenbau GmbH (Paderborn, Germany), Manesty (Merseyside, Great Britain), Vector Corporation (Marion, Iowa, USA), Aeromatic-Fielder AG (Bubendorf, Switzerland), GEA Process Engineering (Hampshire, Great Britain), Fluid Air Inc. (Aurora, Ill., USA), Heinen Systems GmbH (Varel, Germany), Huttlin GmbH (Steinen, Germany), Umang Pharmatech Pvt. Ltd. (Maharashtra, India) and Innojet Technologies (Lörrach, Germany).

By a "solution" is meant within the meaning of the invention a solution in which the ionic liquid and optionally further, possibly catalytically active additives are present dissolved in a corresponding solvent. By a "suspension" is meant according to the invention a suspension in which the ionic liquid is present. By an "emulsion" is meant according to the invention an emulsion in which the ionic liquid is present in liquid form in a further liquid.

By a "support material" is meant within the meaning of the present invention all conceivable materials which can be fluidized in a fluidized bed, irrespective of their composition, shape, size or morphology. The support material can be present in powder form, but it can also be a solid shaped body of any type, such as for example tablets, spheres, cones, rings, strands, hollow strands, trilobes, solid cylinders, hallow cylinders or grit. The support material can have catalytic properties, such as for instance a pre-formed heterogeneous catalyst, or can also be inert.

The support material can be used in suspension processes as powder with high yields and selectivities. Typical particle sizes of such powders are 10 to 250 µm, but particles much smaller than 1 µm can also be used, for instance when soot is used.

Shaped bodies as support material according to aspects of the invention are preferably used for example in catalyst processes operated in a fixed bed. Preferred shaped bodies are those already named above with characteristic diameters of from 0.5 to 18 mm or also monoliths and similar structured packings (cf. Ullmann's Enzyklopädie, $6^{th}$ Edition, 2000 Electronic Release, Chapter Fixed-Bed Reactors, Par. 2: Catalyst for fixed-bed reactors).

It was established that, if the support material itself is a heterogeneous porous catalyst, the activity of the catalyst can be reduced so greatly by coating it with an ionic liquid that shaped bodies with a diameter of up to 2 cm, i.e. shaped bodies with larger dimensions in the range of from 1 mm to 2 cm, more preferably 3 mm to 1.5 cm, even more preferably 8 mm to 1.3 cm, can also be used, without having to accept significant losses in respect of product selectivity. This is guaranteed in particular by the uniform shell thickness and the homogeneous distribution which is obtained only by the method according to the invention. Preferred shaped bodies therefore have a diameter or dimensions of from 1 mm to 2 cm, preferably from 2 mm to 1.8 cm, preferably from 4 mm to 1.5 cm and more preferably from 6 mm to 1.2 cm.

The support material according to aspects of the invention can be any material which can be coated with an ionic liquid. The support material preferably comprises a material selected from the group consisting of titanium oxide, silicon oxide, aluminium oxide, zirconium oxide, magnesium oxide, silicon carbide, magnesium silicate, zinc oxide, zeolites and nanomaterials, such as for example carbon nanotubes or carbon nanofibres, preferably when the support material itself is a heterogeneous catalyst. The above-named oxidic support materials can preferably be used for example in the form of mixed oxides or a defined composition, such as for example $TiO_2$, $SiO_2$, $Al_2O_3$, $ZrO_2$, MgO, $SiC_2$ or ZnO. Furthermore, soots, acetylene black, charcoal, graphite, hydrotalcites or further support materials known per se to a person skilled in the art can preferably be used in different possible modifications. The support materials can preferably be doped for instance with alkali or alkaline earth metals or also with phosphorus, halide and/or sulphate salts. In general, the acid/base properties are modified by such dopings, which can have a positive effect on the catalytic properties.

In addition, the support material according to aspects of the invention can also be a heterogeneous bulk catalyst or supported catalyst, such as for example compositions with variable contents of copper/zinc oxide/aluminium oxide, copper/zinc oxide, copper/chromium oxide, copper/chromium oxide/silicon dioxide, copper/chromium oxide/manganese oxide, cobalt/silicon dioxide, cobalt/diatomaceous earth, nickel/aluminium oxide, nickel/silicon dioxide, nickel/diatomaceous earth, palladium/activated charcoal, platinum/activated charcoal, palladium/graphite, palladium/aluminium oxide, palladium/silver/aluminium oxide, palladium/calcium carbonate, palladium/barium sulphate, platinum/aluminium oxide, rhodium/activated charcoal, rhodium/aluminium oxide, iridium/calcium carbonate, ruthenium/activated charcoal, ruthenium/graphite, gold/titanium oxide or mixtures or alloys of the metals palladium, platinum, silver, gold, rhodium, iridium in an undetermined ratio on one of the support materials activated charcoal, graphite, silicon dioxide, aluminium dioxide, diatomaceous earth, titanium oxide, cerium oxide, zirconium oxide. The catalysts can preferably be doped for instance with alkali or alkaline earth metal salts or oxides, or also with phosphorus, halide and/or sulphate salts. In general, the acid/base properties are modified by such dopings, which can have a positive effect on the catalytic properties.

By spray impregnation within the meaning of the invention is meant any possible way of applying a solution, suspension or emulsion to the support material by atomization, for example through a spraying nozzle.

According to a further embodiment of the present invention, the solution of the method according to the invention preferably contains a catalytically active component or a precursor compound thereof. The catalytically active component is preferably a homogeneous catalyst or metal nanoparticle for example of the metals palladium, rhodium, iridium, platinum, copper, silver, gold, ruthenium, iron as well as mixtures or alloys thereof. Homogeneous catalysts can be all compounds known to a person skilled in the art which are suitable for the catalysis of a chemical reaction in homogeneous phase.

In a further embodiment of the present invention, the support material preferably comprises a catalytically active material. Possible catalytically active materials are those named further above.

In a further embodiment according to aspects of the invention, the solution of the method according to the invention preferably contains at least one further additive. Preferred additives are the following: ligands such as mono-, bi- or tridentate amines, phosphanes, arsanes or stibanes with mixed functionalities, also Brønstedt acids or bases, Lewis acids or bases, salts such as LiBr, CsBr, $CaCl_2$ as well as metal oxides.

As already stated further above, in a further embodiment the support material in the method according to aspects of the invention is preferably fluidized in the fluidized bed with the help of a process gas. By a process gas is meant the gas which makes it possible to swirl the support material in the fluidized bed reactor or fluid bed reactor or to cause it to flow. The process gas can be a reactive gas or also an inert gas. Oxygen, including in the form of air, or hydrogen come into consideration as reactive gases. Hydrogen, or forming gas (mixture of $N_2$ and $H_2$), come into consideration as process gas in particular when the catalyst support contains a catalytically active metal which is either to be reduced from a precursor compound to the elemental metal, or when the already present elemental metal is not to be reoxidized. All known inert gases can be used as inert gas, preferably nitrogen, argon, helium, neon, particularly preferably nitrogen or argon. In a further embodiment according to aspects of the invention, the spray impregnation preferably takes place at a temperature in the range of from 20 to 140° C., particularly preferably in the range of from 30 to 100° C., more preferably in the range of from 35 to 80° C. and most preferably in the range of from 35 to 70° C. In its extremely preferred embodiment, the spray impregnation takes place at a temperature in the range of from 40 to 60° C. It is disadvantageous if the temperature is too high, as here the vapour pressure of the ionic liquid increases, leading to losses in yield. If the temperature is too low, the viscosity is too high and the surface tension is too strong, with the result that the ionic liquid is not distributed homogeneously in a uniform shell thickness over the support body.

According to a further preferred embodiment of a method according to aspects of the invention, the support material is heated, for example by means of heated process air, during application of the solutions. The drying-off speed of the applied solutions can be determined via the degree of heating of the support material. At relatively low temperatures for example the drying-off speed is relatively low, with the result that with a corresponding quantitative application, greater shell thicknesses can result because of the high diffusion of the precursor compounds due to the occurrence of solvent. At relatively high temperatures the drying-off speed for example is relatively high, with the result that the solvent of the solution coming into contact with the support material almost immediately dries off, which is why solution applied to the support material cannot penetrate deep into the latter. At relatively high temperatures relatively small shell thicknesses can thus be obtained when there is a high ionic liquid loading.

In a further embodiment of the present invention, the spray impregnation is preferably carried out at a pressure in the range of from 0.1 to 3 bar, particularly preferably in the range of from 0.5 to 2 bar, more preferably in the range of from 0.8 to 1.5 bar, extremely preferably in the range of from 0.9 to 1.1 bar. It is disadvantageous if the pressure is too high, as here the viscosity and surface tension increase. Too low a pressure increases the vapour pressure of the ionic liquid, with the result that losses in yield may result.

In a further embodiment according to aspects of the invention, the ionic liquid is present in the solution preferably in a range of from 1 to 10 wt.-%, relative to the total weight of the solution, more preferably 1.5 to 8 wt.-%, even more preferably 2 to 6 wt.-% and most preferably 3 to 5 wt.-%. Too low a concentration of ionic liquid increases the spraying time in the fluid bed or in the fluidized bed needed to apply the same quantity of ionic liquid. Too high a concentration results in coatings with non-homogeneous shell thickness.

All solvents that are capable of solvating anions and cations accordingly and thereby dissolving them come into consideration as solvents for the ionic liquids. Polar solvents are particularly preferably used here, such as for example water, DMSO, acetone, isopropanol, ethanol, methanol, acetonitrile, dichloromethane, tert-butyl methyl ether, DMF or mixtures thereof, wherein water is particularly preferred.

In a further embodiment of the present invention, the spray impregnation is preferably carried out at a delivery rate in the range of from 0.01 to 0.2 ml solution per minute per gram support material, more preferably in the range of from 0.03 to 0.15 ml solution per minute per gram support material, even more preferably 0.05 to 1.2 ml solution per minute per gram support material and most preferably in the range of from 0.06 to 0.09 ml solution per minute per gram support material. In other words, this is taken to mean that a particular quantity of solution per minute for a particular quantity of support material is applied to the support material by spray impregnation. Too high a delivery rate results in a non-homogeneous shell thickness. Too low a delivery rate is time-consuming and cost-intensive.

The composite material is preferably dried after the spray impregnation at a temperature of ≥40° C., particularly preferably ≥45° C. and most preferably ≥50° C.

In yet another embodiment, it can also be preferred that the BET surface area of the support material without the coating with an ionic liquid is 1 to 1000 m$^2$/g, preferably 1 to 600 m$^2$/g, particularly preferably 1 to 400 m$^2$/g. The BET surface area is determined using the single-point method by adsorption of nitrogen in accordance with DIN 66132.

It can furthermore be preferred that the BET surface area of the support material with the coating of the ionic liquid (IL=ionic liquid) is 1 to 900 m$^2$/g, preferably 1 to 550 m$^2$/g, particularly preferably 1 to 380 m$^2$/g.

In addition, it can be preferred that the integral pore volume of a support material (determined in accordance with DIN 66133 (Hg porosimetry) without the IL coating is greater than 0.1 ml/g, preferably greater than 0.18 ml/g.

According to a preferred embodiment of the composite material according to aspects of the invention, at most 10% of the pore volume of the support material without the IL coating is formed from pores with a radius smaller than 2 nm, preferably 8%, preferably at most 6% and particularly preferably at most 5%. A larger proportion of pores that are too small results in undesired non-homogeneous coating, as small pores are more difficult to fill due to the strong surface tension and viscosity of ionic liquids.

According to a further preferred embodiment of the composite material according to aspects of the invention, at most 10% of the pore volume of the support material without the IL coating is formed from pores with a radius greater than 500 nm, preferably at most 8%, preferably at most 6% and particularly preferably at most 5%. In a further preferred embodiment of the composite material according to the invention, it is provided that the average pore diameter of the support material without the IL coating is 10 to 100 nm. Too large a proportion of large pores is also disadvantageous, as the ionic liquid preferably collects here, likewise resulting in a non-homogeneous coating.

In addition, according to a preferred development of the composite material according to aspects of the invention, the average pore diameter of the support material with the IL coating can be 3 to 100 nm.

In principle, within the framework of the present invention the catalyst according to aspects of the invention can be coated with any ionic liquid and the cation can accordingly be of any type. Generally, for example ammonium or phosphonium ions or cations which contain at least one five- or six-membered heterocycle which has at least one phosphorus or nitrogen atom as well as optionally an oxygen atom or sulphur atom are preferred as cation. Cations which contain at least one five- or six-membered heterocycle which has one, two or three nitrogen atoms and a sulphur or oxygen atom are particularly preferred. Cations which contain at least one five- or six-membered heterocycle which has one or two nitrogen atoms are quite particularly preferred.

It can be preferred that the cation of the ionic liquid is selected from compounds of the following general formulae IL-1 to IL-23:

(IL-1)

(IL-2)

-continued
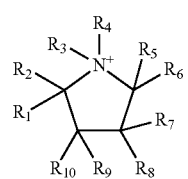 (IL-3)
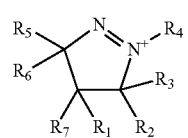 (IL-4)
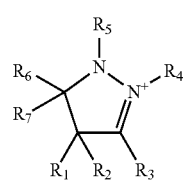 (IL-5)
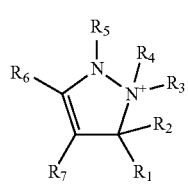 (IL-6)
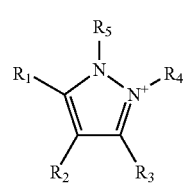 (IL-7)
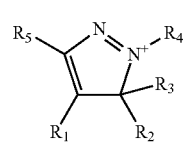 (IL-8)
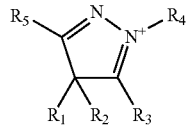 (IL-9)
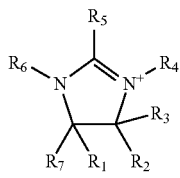 (IL-10)
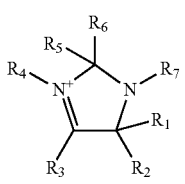 (IL-11)
-continued
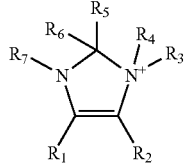 (IL-12)
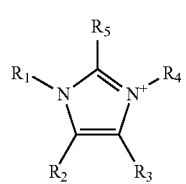 (IL-13)
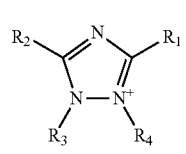 (IL-14)
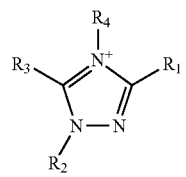 (IL-15)
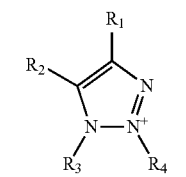 (IL-16)
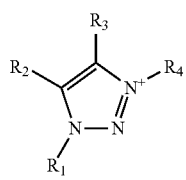 (IL-17)
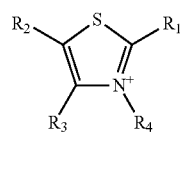 (IL-18)
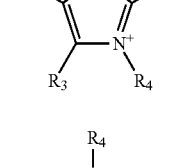 (IL-19)
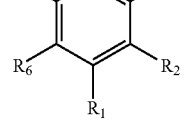 (IL-20)

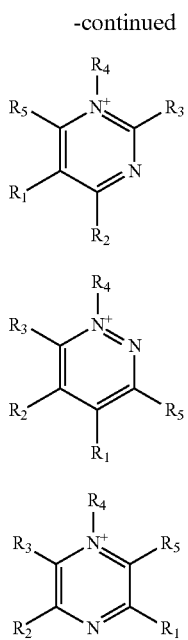

(IL-21)

(IL-22)

(IL-23)

in which the radicals $R_1$, $R_2$, $R_3$, $R_4$, $R_5$, $R_6$, $R_7$, $R_8$, $R_9$ and $R_{10}$ can in each case independently of each other be radicals selected from the group consisting of hydrogen, functional groups, aryl, alkyl, aryloxy, alkyloxy, halogen, heteroatom- and/or heterocycle-substituted $C_1$-$C_{18}$ alkyl, $C_2$-$C_{18}$ alkyl interrupted by one or more non-adjacent oxygen atoms and/or sulphur atoms and/or one or more substituted or unsubstituted imino groups, $C_6$-$C_{12}$ aryl interrupted by one or more non-adjacent oxygen atoms and/or sulphur atoms and/or one or more substituted or unsubstituted imino groups, $C_5$-$C_{12}$ cycloalkyl interrupted by one or more non-adjacent oxygen atoms and/or sulphur atoms and/or one or more substituted or unsubstituted imino groups, a five- to six-membered heterocycle containing oxygen, nitrogen and/or sulphur atoms,
wherein two of the named radicals can be linked to each other accompanied by formation of an unsaturated or saturated ring segment which can optionally be interrupted by one or more oxygen and/or sulphur atoms and/or one or more substituted or unsubstituted imino groups, wherein the ring segment can be substituted by functional groups, aryl, alkyl, aryloxy, alkyloxy, halogen, heteroatom and/or heterocycle radicals,
and wherein $R_4$ can in addition be selected from the group of radicals consisting of $C_1$-$C_{18}$ alkyloyl, $C_1$-$C_{18}$ alkyloxycarbonyl, $C_5$-$C_{12}$ cycloalkylcarbonyl and $C_6$-$C_{12}$ aryloyl, wherein the members of the named group can in each case be substituted by one or more functional groups, aryl, alkyl, aryloxy, alkyloxy, halogen, heteroatoms and/or heterocycle radicals, wherein $C_1$-$C_{18}$, $C_5$-$C_{12}$, or $C_6$-$C_{12}$ refer to the alkyl chain.

In this, the term functional groups means the group of the following functional groups: aryl-, alkyl-, aryloxy-, alkyloxy-, halogen-, heteroatom- and/or heterocycle-substituted $C_1$-$C_{18}$ alkyl, for example methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethylpropyl, 1,1-dimethylbutyl, 1,1,3,3-tetramethylbutyl, benzyl, 1-phenylethyl, 2-phenylethyl, alpha-alpha-dimethylbenzyl, benzhydryl, p-tolylmethyl, 1-(p-butyl-phenyl)-ethyl, p-chlorobenzyl, 2,4-dichlorobenzyl, p-methoxybenzyl, m-ethoxybenzyl, 2-cyanoethyl, 2-cyanopropyl, 2-methoxycarbonethyl, 2-ethoxycarbonylethyl, 2-butoxycarbonylpropyl, 1,2-di-(methoxycarbonyl)-ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, $C_2$-$C_{18}$ alkyl interrupted by one or more non-adjacent oxygen and/or sulphur atoms and/or one or more substituted or unsubstituted imino groups, for example 5-hydroxy-3-oxa-pentyl, 8-hydroxy-3,6-dioxa-octyl, 11-hydroxy-3,6,9-trioxa-undecyl, 7-hydroxy-4-oxa-heptyl, 11-hydroxy-4,8-dioxa-undecyl, 15-hydroxy-4,8,12-trioxa-pentadecyl, 9-hydroxy-5-oxa-nonyl, 14-hydroxy-5,10-oxa-tetradecyl, 5-methoxy-3-oxa-pentyl, 8-methoxy-3,6-dioxa-octyl, 11-methoxy-3,6,9-trioxa-undecyl, 7-methoxy-4-oxa-heptyl, 11-methoxy-4,8-dioxa-undecyl, 15-methoxy-4,8,12-trioxa-pentadecyl, 9-methoxy-5-oxa-nonyl, 14-methoxy-5,10-oxa-tetradecyl, 5-ethoxy-3-oxa-pentyl, 8-ethoxy-3,6-dioxa-octyl, 11-ethoxy-3,6,9-trioxa-undecyl, 7-ethoxy-4-oxa-heptyl, 11-ethoxy-4,8-dioxa-undecyl, 15-ethoxy-4,8,12-trioxa-pentadecyl, 9-ethoxy-5-oxa-nonyl and 14-ethoxy-5,10-oxa-tetradecyl.

If two radicals form a ring with each other, these radicals together can preferably mean 1,3-propylene, 1,4-butylene, 2-oxa-1,3-propylene, 1-oxa-1,3-propylene, 2-oxa-1,3-propylene, 1-oxa-1,3-propenylene, 1-aza-1,3-propenylene, 1-$C_1$-$C_4$-alkyl-1-aza-1,3-propenylene, 1,4-buta-1,3-dienylene, 1-aza-1,4-buta-1,3-dienylene or 2-aza-1,4-buta-1,3-dienylene.

The number of oxygen and/or sulphur atoms and/or imino groups in the preferred cations of the ionic liquid is not limited. In general, it is not more than 5 per radical, preferably not more than 4, in particular not more than 3. Furthermore, there is at least one carbon atom, particularly preferably at least two, between two heteroatoms.

Preferred imino groups can for example be imino, methylimino, iso-propylimino, n-butylimino or tert-butylimino.

Furthermore, the term functional groups means the group of the following functional groups: carboxy, carboxamide, hydroxy, di-($C_1$-$C_4$-alkyl)amino, $C_1$-$C_4$-alkyloxycarbonyl, cyano, $C_1$-$C_4$-alkyloxy, $C_6$-$C_{12}$ aryl substituted by functional groups, aryl, alkyl, aryloxy, alkyloxy, halogen, heteroatoms and/or heterocycles, for example phenyl, tolyl, xylyl, alpha-naphthyl, beta-naphthyl, 4-diphenylyl, chlorophenyl, dichlorophenyl, trichlorophenyl, difluorophenyl, methylphenyl, dimethylphenyl, trimethylphenyl, ethylphenyl, diethylphenyl, iso-propylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-diethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxyethylphenyl, $C_5$-$C_{12}$ cycloalkyl substituted by functional groups, aryl, alkyl, aryloxy, alkyloxy, halogen, heteroatoms and/or heterocycles, for example cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl or dichlorocyclopentyl, saturated or unsaturated bicyclic systems, e.g. norbornyl or norbornenyl, a five- to six-membered heterocycle containing oxygen, nitrogen and/or sulphur atoms, for example furyl, thiophenyl, pyrryl, pyridyl, indolyl, benzoxazolyl, dioxolyl, dioxyl, benzimidazolyl, benzthiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl, and a $C_1$-$C_4$ alkyl, for example methyl, ethyl, propyl, isopropyl, n-butyl, sec-butyl or tert-butyl.

$C_1$-$C_{18}$ alkyloyl (alkylcarbonyl) can be for example acetyl, propionyl, n-butyloyl, sec-butyloyl, tert-butyloyl, 2-ethylhexylcarbonyl, decanoyl, dodecanoyl, chloroacetyl, trichloroacetyl or trifluoroacetyl.

$C_1$-$C_{18}$ alkyloxycarbonyl can be for example methyloxycarbonyl, ethyloxycarbonyl, propyloxycarbonyl, isopropyloxycarbonyl, n-butyloxycarbonyl, sec-butyloxycarbonyl, tert-butyloxycarbonyl, hexyloxycarbonyl, 2-ethylhexyloxycarbonyl or benzyloxycarbonyl.

$C_5$-$C_{12}$ cycloalkylcarbonyl can be for example cyclopentylcarbonyl, cyclohexylcarbonyl or cyclododecylcarbonyl.

$C_5$-$C_{12}$ aryloyl (arylcarbonyl) can be for example benzoyl, toluyl, xyloyl, alpha-naphthoyl, beta-naphthoyl, chlorobenzoyl, dichlorobenzoyl, trichlorobenzoyl or trimethylbenzoyl.

$R_1$, $R_2$, $R_3$, $R_5$, $R_6$, $R_7$, $R_8$, $R_9$ and $R_{10}$, in each case independently of each other, are preferably hydrogen, methyl, ethyl, n-butyl, 2-hydroxyethyl, 2-cyanoethyl, 2-(methoxycarbonyl)-ethyl, 2-ethoxycarbonyl-ethyl, 2-n-butoxycarbonyl-ethyl, dimethylamino, diethylamino or chlorine.

$R_4$ is preferably methyl, ethyl, n-butyl, 2-hydroxyethyl, 2-cyanoethyl, 2-methoxycarbonyl-ethyl, 2-ethoxycarbonyl-ethyl, 2-n-butoxycarbonyl-ethyl, acetyl, propionyl, t-butyryl, methoxycarbonyl, ethoxycarbonyl or n-butoxycarbonyl.

Particularly preferred ammonium ions (IL-1) are those in which, independently of each other, $R_4$ is selected from acetyl, methyl, ethyl or n-butyl and $R_1$, $R_2$ and $R_3$ are selected from methyl, ethyl, n-butyl, 2-hydroxyethyl, benzyl or phenyl.

Particularly preferred phosphonium ions (IL-2) are those in which, independently of each other, $R_4$ is selected from acetyl, methyl, ethyl or n-butyl and $R_1$, $R_2$ and $R_3$ are selected from phenyl, phenoxy, ethoxy and n-butoxy.

Particularly preferred pyrrolidinium ions (IL-3) are those in which, independently of each other, $R_3$ and $R_4$ are selected from acetyl, methyl, ethyl or n-butyl and all other radicals mean hydrogen.

Particularly preferred 1-pyrazolinium ions (IL-4) are those in which, independently of each other, all radicals apart from $R_4$ are selected from hydrogen or methyl and $R_4$ is selected from acetyl, methyl, ethyl or n-butyl.

Particularly preferred 2-pyrazolinium ions (IL-5) are those in which, independently of each other, $R_5$ is selected from hydrogen, methyl, ethyl or phenyl, $R_4$ is selected from acetyl, methyl, ethyl or n-butyl and the remaining radicals are selected from hydrogen or methyl.

Particularly preferred 3-pyrazolinium ions (IL-6) are those in which, independently of each other, $R_3$ and $R_5$ are selected from hydrogen, methyl, ethyl or phenyl, $R_4$ is selected from acetyl, methyl, ethyl or n-butyl and the remaining radicals are selected from hydrogen or methyl.

Particularly preferred 1H-pyrazolium ions (IL-7) are those in which, independently of each other, $R_5$ is selected from hydrogen, methyl or ethyl, $R_1$, $R_2$ and $R_3$ are selected from hydrogen or methyl and $R_4$ is selected from acetyl, methyl, ethyl or n-butyl.

Particularly preferred 3H-pyrazolium ions (IL-8) are those in which, independently of each other, $R_2$ is selected from hydrogen, methyl or ethyl, $R_1$, $R_3$ and $R_5$ are selected from hydrogen or methyl and $R_4$ is selected from acetyl, methyl, ethyl or n-butyl.

Particularly preferred 4H-pyrazolium ions (IL-9) are those in which, independently of each other, $R_1$ $R_2$, $R_3$ and $R_5$ are selected from hydrogen or methyl and $R_4$ is selected from acetyl, methyl, ethyl or n-butyl.

Particularly preferred imidazolinium ions (IL-10) are those in which, independently of each other, $R_5$ or $R_6$ is selected from hydrogen, methyl or ethyl, $R_4$ is selected from acetyl, methyl, ethyl or n-butyl and the remaining radicals are selected from hydrogen or methyl.

Particularly preferred imidazolinium ions (IL-11) are those in which, independently of each other, $R_5$, $R_6$ or $R_7$ is selected from hydrogen, methyl or ethyl, $R_4$ is selected from acetyl, methyl, ethyl or n-butyl and the remaining radicals are selected from hydrogen or methyl.

Particularly preferred imidazolinium ions (IL-12) are those in which, independently of each other, $R_3$ or $R_7$ is selected from hydrogen, methyl, ethyl, n-butyl or phenyl, $R_4$ is selected from acetyl, methyl, ethyl or n-butyl and $R_5$ or $R_6$ is selected from hydrogen, methyl or ethyl and $R_1$ or $R_2$ is selected from hydrogen or methyl.

Particularly preferred imidazolium ions (IL-13) are those in which, independently of each other, $R_1$ is selected from the group consisting of methyl, ethyl, n-propyl, n-butyl, n-pentyl, n-octyl, n-decyl, n-dodecyl, 2-hydroxyethyl and 2-cyanoethyl, $R_4$ is selected from acetyl, methyl, ethyl or n-butyl and the remaining radicals, independently of each other, are selected from hydrogen, methyl or ethyl.

Particularly preferred 1,2,4-triazolium ions (IL-14) and (IL-15) are those in which, independently of each other, $R_1$ or $R_2$, or $R_1$ or $R_3$, is selected from hydrogen, methyl, ethyl or phenyl, $R_4$ is selected from acetyl, methyl, ethyl or n-butyl and $R_3$ or $R_2$ is selected from hydrogen, methyl or phenyl.

Particularly preferred 1,2,3-triazolium ions (IL-16) and (IL-17) are those in which independently of each other, $R_3$ or $R_1$ is selected from hydrogen, methyl or ethyl, $R_4$ is selected from acetyl, methyl, ethyl or n-butyl and $R_1$ or $R_2$, or $R_2$ or $R_3$, is selected from hydrogen or methyl, or $R_1$ and $R_2$, or $R_2$ and $R_3$, are 1,4-buta-1,3-dienylene and all other radicals are hydrogen.

Particularly preferred thiazolium ions (IL-18) or oxazolium ions (IL-19) are those in which, independently of each other, $R_1$ is selected from hydrogen, methyl, ethyl or phenyl, $R_4$ is selected from acetyl, methyl, ethyl or n-butyl and $R_2$ or $R_3$ is selected from hydrogen or methyl.

Particularly preferred pyridinium ions (IL-20) are those in which one of the radicals $R_1$, $R_2$, $R_3$, $R_5$ and $R_6$ is methyl, ethyl or chlorine, $R_4$ is acetyl, methyl, ethyl or n-butyl and all other radicals are hydrogen, or $R_1$ is dimethylamino, $R_4$ is acetyl, methyl, ethyl or n-butyl and all other radicals are hydrogen or $R_4$ is acetyl, methyl, ethyl or n-butyl and all other radicals are hydrogen or $R_2$ is carboxy or carboxamide, $R_4$ is acetyl, methyl, ethyl or n-butyl and all other radicals are hydrogen or $R_2$ and $R_3$ or $R_2$ and $R_1$ are 1,4-buta-1,3-dienylene, $R_4$ is acetyl, methyl, ethyl or n-butyl and all other radicals are hydrogen.

Particularly preferred pyrimidinium ions (IL-21) are those in which $R_1$, $R_4$ and $R_5$ are hydrogen or methyl, $R_4$ is acetyl, methyl, ethyl or n-butyl and $R_3$ is hydrogen, methyl or ethyl, or $R_2$ and $R_5$ are methyl, $R_1$ is hydrogen and $R_3$ is hydrogen, methyl or ethyl and $R_4$ is acetyl, methyl, ethyl or n-butyl.

Particularly preferred pyridazinium ions (IL-22) are those in which one of the radicals $R_1$, $R_2$, $R_3$ and $R_5$ is methyl or ethyl, $R_4$ is acetyl, methyl, ethyl or n-butyl and all other radicals are hydrogen or $R_4$ is acetyl, methyl, ethyl or n-butyl, and all other radicals are hydrogen.

Particularly preferred pyrazinium ions (IL-23) are those in which $R_1$, $R_2$, $R_3$ and $R_5$ are all methyl and $R_4$ is acetyl, methyl, ethyl or n-butyl or $R_4$ is acetyl, methyl, ethyl or n-butyl and all other radicals are hydrogen.

Of the above-mentioned cation groups IL-1 to IL-23, the named ammonium, phosphonium, pyridinium and imidazolium ions are particularly preferred.

1,2-Dimethylpyridinium, 1-methyl-2-ethylpyridinium, 1-methyl-2-ethyl-6-methylpyridinium, N-methylpyridinium, 1-butyl-2-methylpyridinium, 1-butyl-2-ethylpyridinium, 1-butyl-2-ethyl-6-methylpyridinium, N-butylpyridinium, 1-butyl-4-methylpyridinium, 1,3-dimethylimidazoliunn, 1,2,3-trimethylinnidazoliurn, 1-n-butyl-3-methylimdazolium, 1,3,4,5-tetramethylimidazolium, 1,3,4-trimethylimidazolium, 2,3-dimethylimidazolium, 1-butyl-2,3-dimethylimidazolium, 3,4-dinnethylimidazolium, 2-ethyl-3,4-dimethylimidazoliunn, 3-methyl-2-ethylimidazole, 3-butyl-1-methylimidazolium, 3-butyl-1-ethylimidazolium, 3-butyl-1,2-dimeraylimidazolium, 1,3-di-n-butylimidazolium, 3-butyl-1,4,5-trimethylimidazolium, 3-butyl-1,4-dimethylimidazolium, 3-butyl-2-methylimidazolium, 1,3-dibutyl-2-methylimidazolium, 3-butyl-4-methylimidazolium, 3-butyl-2-ethyl-4-methylimidazolium and 3-butyl-2-ethylimidazolium, 1-methyl-3-octylimidazolium, 1-decyl-3-methylimidazolium are quite particularly preferred as cations.

1-Butyl-4-methylpyridinium, 1-n-butyl-3-methylimidazolium and 1-n-butyl-3-ethylimidazolium are preferred in particular.

Cations which are derived from diazabicyclononene or diazabicycloundecene are also possible.

Analogously to the above embodiments, the anion of the ionic liquid can be of any type. However, it is preferred if the anion of the ionic liquid is selected from the group consisting of $F^-$, $Cl^-$, $Br^-$, $I^-$, $PF_6^-$, $BF_4^-$, alkyl sulphate, preferably a $C_1$ to $C_{18}$ alkyl sulphate, ether sulphate, acetate, trifluoroacetate, triflate, nonaflate, sulphate, hydrogen sulphate, methyl sulphate, ethyl sulphate, sulphite, hydrogen sulphite, aluminium chlorides, preferably $AlCl_4^-$, $Al_2Cl_7^-$ or $Al_3Cl_{10}^-$, aluminium tribromide, nitrite, nitrate, metal complexes, for example metal halides such as copper chloride $CuCl_2^-$, phosphates, phosphate, hydrogen phosphate, dihydrogen phosphate, dimethyl phosphonate, diethyl phosphonate, tris(pentafluoroethyl)trifluorophosphates, carbonate, hydrogen carbonate, methyl carbonate, sulphonate, tosylate, bis(trifluoromethylsulphonyl)imide, dicyanamide, tetracyanoborate, cyanide, isocyanate and isothiocyanate.

By ether sulphates are meant existing compounds of the general formula

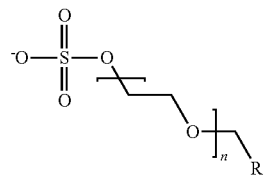

in which n is an integer from 1 to 8 and R is an alkyl radical from $C_1$ to $C_{18}$.

As already described further above, the solution, emulsion or suspension, preferably solution, with the ionic liquid and the further optional additives is sprayed into the fluidized bed of a fluidized bed apparatus or the fluid bed of a fluid bed apparatus. The constituents of the solution, emulsion or liquid, in particular the ionic liquid, are kept in the fluidized bed or fluid bed of the apparatus by the swirling with a process gas. The support material is likewise located in the fluidized bed or fluid bed of the fluidized bed apparatus or the fluid bed apparatus. In this way, almost all of the ionic liquid or optional additives sprayed in with the solution, emulsion or suspension can be applied to the surface of the support material, with the result that the method according to the invention has the advantage that the method can be carried out with small losses of ionic liquid or the optional additives. In addition, the method can be carried out more quickly than conventional methods and is reproducible and free of wastewater. As ionic liquids normally have a very strong surface tension, it was hitherto believed that in a gas stream they tend to agglomerate after the atomization in the course of the swirling in the fluidized bed or fluid bed apparatus, with the result that it was assumed that such a method is not suitable for applying ionic liquids homogeneously to surfaces of support materials, in particular support materials with a complex shape. It was surprisingly found with the help of the method according to the invention that these disadvantages do not occur. Thus, through the method according to the invention, the layer thickness and homogeneity of the distribution on the surface of the support material can be set accordingly by corresponding setting of the above-named parameters.

The present invention also relates to a composite material which is obtainable by the above-mentioned method according to the invention. Via its production by means of the method according to the invention, the composite material of the present invention has the advantage that the ionic liquid and any additives located therein, such as for example a homogeneous catalyst located therein, are distributed extremely homogeneously over the surface of the support material.

The present invention furthermore relates to the use of the composite material according to the invention or of the composite material produced in the method according to the invention as synthetic catalyst. The composite material is preferably used as catalyst in the hydrogenation of unsaturated hydrocarbon compounds. This is preferably the catalytic selective hydrogenation of polyunsaturated hydrocarbon compounds. An example of this is the hydrogenation of acetylene to ethylene or, of butadiene to butene.

The following examples are not intended to limit the method according to the invention or the composite material according to the invention, but illustrate it purely by way of example:

EXAMPLES

Example 1 method for impregnating KA-160 support spheres (5 to 6 mm), obtainable from Süd-Chemie AG, with 10 wt.-% of the ionic liquid 1-butyl-2,3-dimethylimidazoliumtriflate (BM-MIM[OTf]) and 14 wt.-% of the homogeneous catalyst [Et₃(Bz)N][Ru(CO)₃Cl₃]:

7 g of the ionic liquid, 3.58 g ruthenium tricarbonyl dichloride and 6.38 g benzyl triethyl ammonium chloride are weighed into a 500-ml round-bottomed flask. 150 g distilled water is added to the mixture. A yellow-coloured solution forms (total mass 167 g). This solution is stirred for 5 minutes in the ultrasound bath and heated to a temperature of 30° C.

70 g of the support material KA-160 is fluidized in the fluidized bed apparatus with the help of air and impregnated with the catalyst solution under different process conditions:
  a) Delivery rate: 5 ml/min
  Process temperature: 80° C.
  Pressure: 1.0 bar After the application of all of the catalyst solution by spray impregnation, the support is dried for a further 30 minutes at 80° C. 87.0 g of a dry yellowish-coloured material is obtained. The results of the determination of the ruthenium and the nitrogen content by elemental analysis are:
  Ru: 1.61% (calculated 1.62%)
  N: 7.21% (calculated 7.22%).

It can be seen from this that the losses of active components (ionic liquid, homogeneous catalyst) are negligibly small. The dry catalysts obtained are examined for the distribution of the ionic liquid (bright areas) as well as of the catalyst complex by means of scanning electron microscopy:

FIG. 1 shows a scanning electron microscopy image in which the distribution of the homogeneous catalyst used is to be seen.

Figure 2:
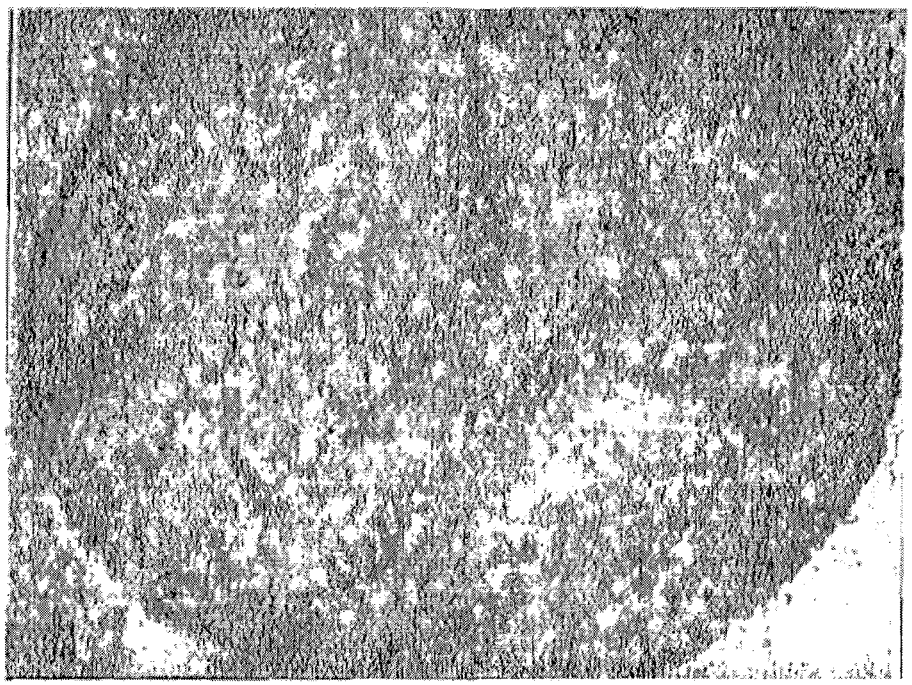
FIG. 2 is a scanning electron microscopy image of the distribution of butyl dimethyl imidazolium triflate of Example 1.

FIG. 2 shows a scanning electron microscopy image in which the distribution of butyl dimethyl imidazolium triflate is to be seen. Under the conditions used, a shell catalyst (egg shell) with a shell thickness of approx. 120 µm is consequently obtained. As can be seen from the comparison of the images in FIGS. 1 and 2, both the ionic liquid and the homogeneous catalyst have identical penetration depths, which suggests a mixture that is even already homogeneous in the solution used.

Example 2

Figure 3:
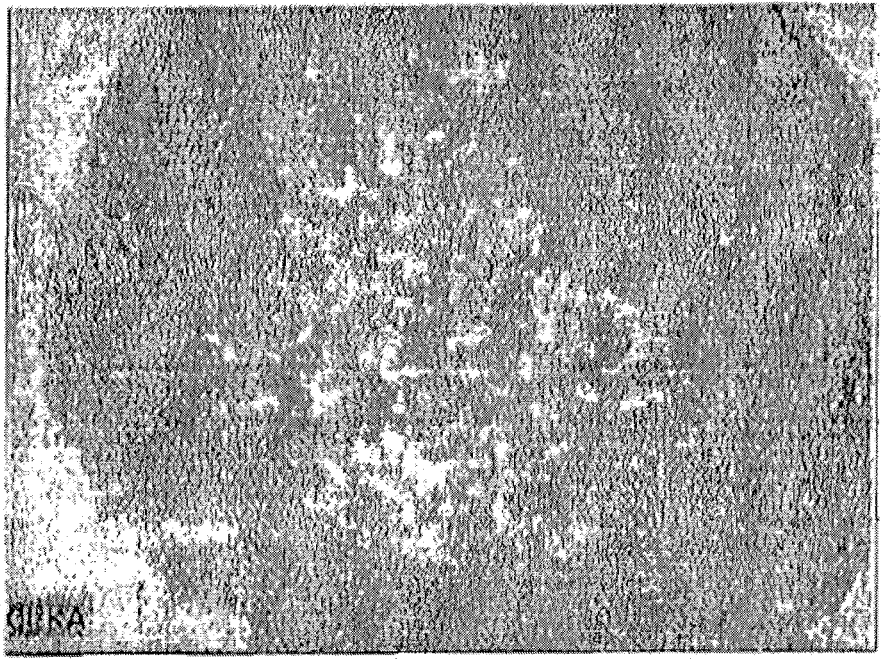
FIG. 3 is a scanning electron microscopy image of the homogeneous catalyst of Example 2.
Figure 4:
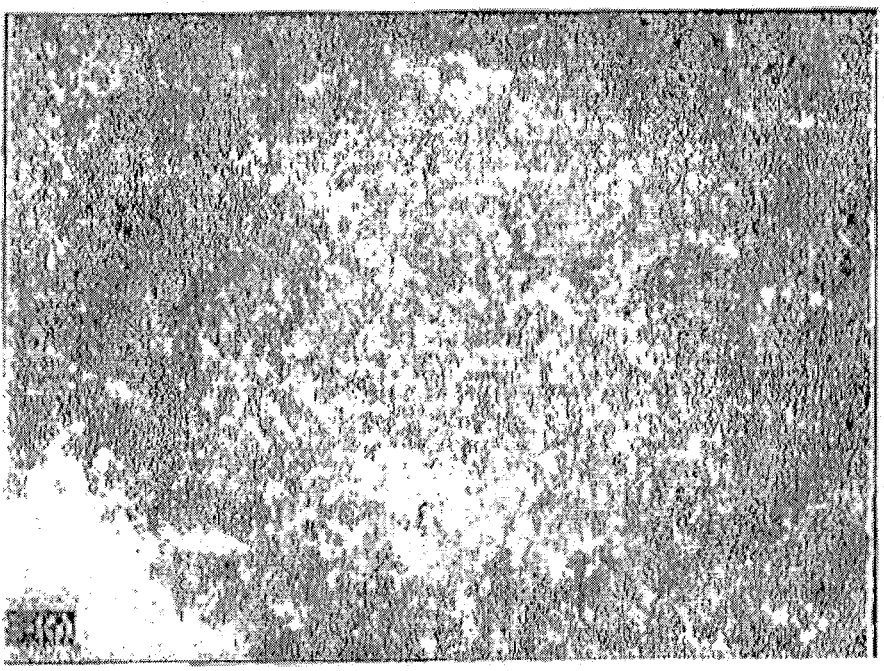
FIG. 4 is a scanning electron microscopy image of the distribution of the ionic liquid of Example 2.

The same method as in Example 1 was carried out, with the difference that the process temperature was reduced to 60° C. The distribution of the homogeneous catalyst can be seen in FIG. 3, which shows a scanning electron microscopy image in which the homogeneous catalyst is to be seen. FIG. 4 shows a scanning electron microscopy image with the distribution of the ionic liquid.

The shell thicknesses to be seen in the images for the ionic liquid and the homogeneous catalyst are 940 or 930 µm respectively.

Example 3

Figure 5:
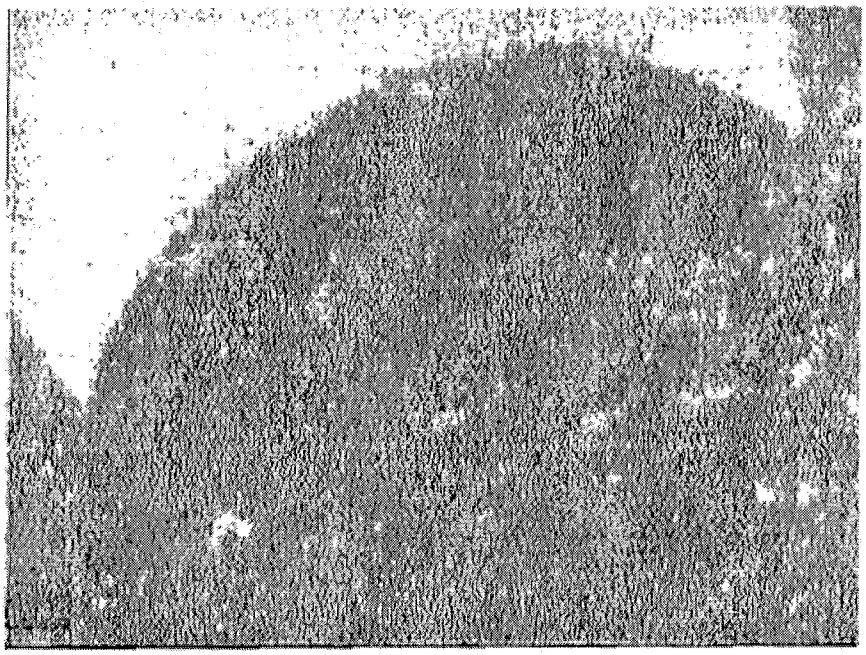
FIG. 5 is a scanning electron microscopy image of the obtained product of Example 3.

The same method as in Example 1 was carried out, with the difference that the process temperature was reduced to 40° C. It can be seen from FIG. 5, which shows a scanning electron microscopy image of the obtained product, that the ionic liquid is distributed extremely homogeneously over the support.

Example 4

The same method as in Example 1 was carried out, with the difference that the spraying pressure was increased to 1.2 bar.

Figure 6:
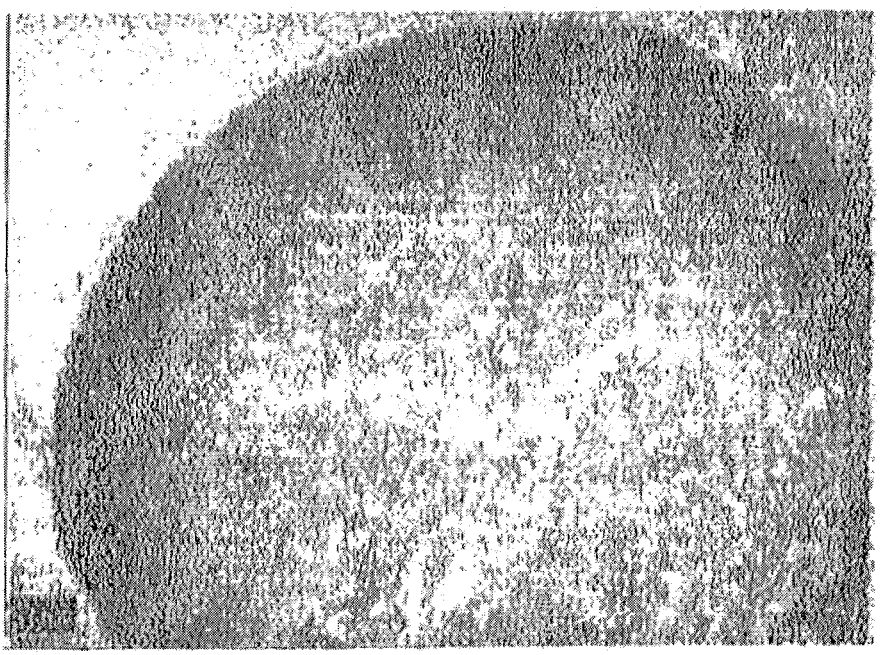
FIG. 6 is a scanning electron microscopy image of the distribution of the ionic liquid on the support of Example 4.

The scanning electron microscopy image shown in FIG. 6 shows the distribution of the ionic liquid on the support.

Example 5

In Example 5, the composite material produced in Example 1 was post-impregnated with water under the following conditions:
  Delivery rate: 5 ml/min
  Process temperature: 80° C.
  Spraying pressure: 1.0 bar
  Water quantity: 150 ml The results or distributions of the components are shown in Table 1.

Example 6

The same post-impregnation as in Example 5 was carried out, with the difference that the impregnation took place twice, with 150 ml water in each case. The results are likewise shown in Table 1.

Example 7

The same post-impregnation as in Example 5 was carried out, with the difference that the impregnation was carried out three times, with 150 ml water each time. The results are likewise shown in Table 1.

Example 8

The same post-impregnation as in Example 5 was carried out, with the difference that the post-impregnation was carried out once, with 500 ml water. The results are shown in Table 1.

Example 9

The same method for producing a composite material as in Example 1 was carried out, with the difference that, instead of 150 ml water, 75 ml water was used. The results are shown in Table 1.

The above-named Examples 1 to 9 show that any distribution of the components on the macroscopic support material can be set by the targeted choice of the process conditions (egg shell, uniform, egg white, egg yolk). In addition, different active components can also be applied in shells by successive impregnations (multiple shells).

Figure 7:
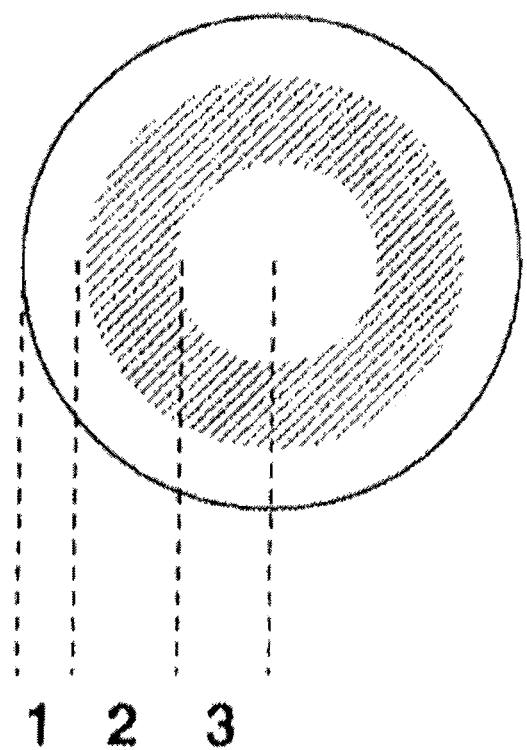
FIG. 7 is a top view of a support sphere of Example 9.

In the following Table 1, distances (R1 to R3) are given which illustrate the distribution of the applied components of Examples 1 to 9 in the support. FIG. 7 shows a top view of a support sphere used with the distances R1 to R3 drawn in in each case, wherein the reference number 1 refers to the distance R1, the reference number 2 to the distance R2 and the reference number 3 to the distance R3. The distance R1 indicates at what depth of the support the corresponding layer begins. The distance R2 indicates the depth of the corresponding layer in the support. The distance R3 indicates how deeply the layer extends into the support. Using Table 1 it can be seen that the higher the temperature is, the thinner the shell is. If the pressure is increased, the shell becomes thicker. Post-impregnation with water forces the layer deeper into the inside of the support.

| Examples | R1 (μm) | R2 (μm) | R3 (μm) |
|---|---|---|---|
| 1 | 0 | 120 | 2680 |
| 2 | 0 | 940 | 1860 |
| 3 | 0 | 2800 | 0 |
| 4 | 0 | 260 | 2540 |
| 5 | 0 | 310 | 2490 |
| 6 | 90 | 350 | 2360 |
| 7 | 250 | 390 | 2160 |
| 8 | 1500 | 1300 | 0 |
| 9 | 0 | 820 | 1980 |

Example 10

Method for impregnating aluminium oxide tablets (CTR 4×4 mm) with 10 wt.-% of the ionic liquid 1-butyl-2,3-dimethylimidazoliumtriflate (BMMIM[OTf]):

7 g of the ionic liquid, 3.58 g ruthenium tricarbonyl dichloride and 6.38 g benzyl triethyl ammonium chloride are weighed into a 500-ml round-bottomed flask. 150 g distilled water is added to the mixture. A yellow-coloured solution forms (total mass 167 g). This is stirred for 5 minutes in the ultrasound bath and lightly heated.

Figure 8:
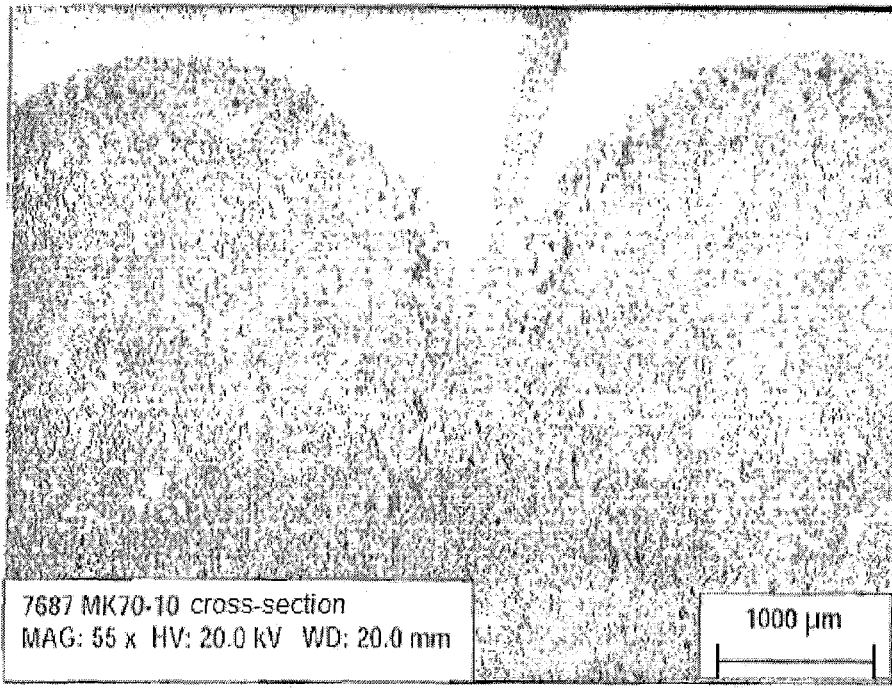
FIG. 8 is a scanning electron microscopy image of the distribution of the ionic liquid on the support of Example 9, in top view.
Figure 9:
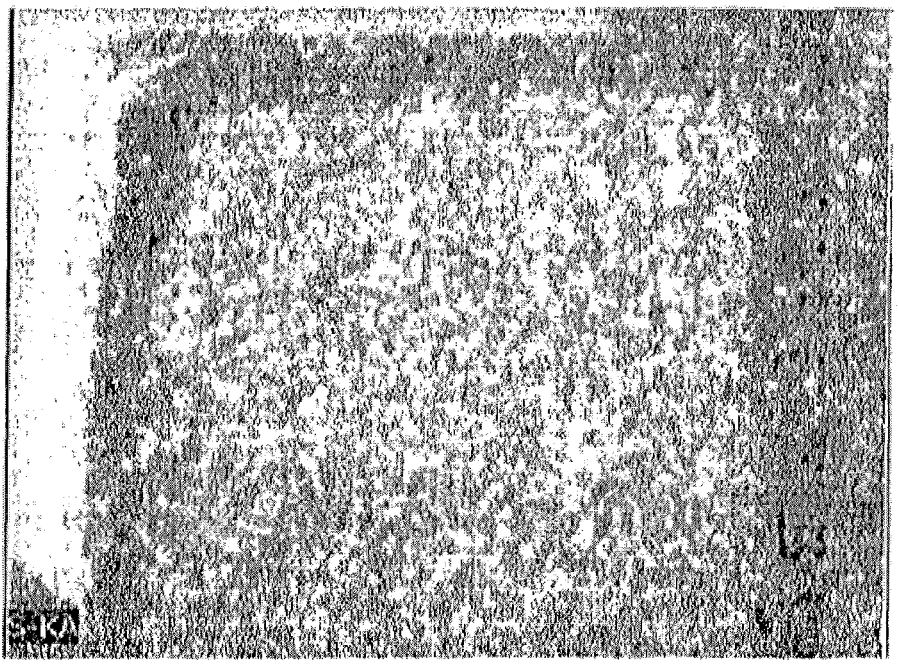
FIG. 9 is a scanning electron microscopy image of the distribution of the ionic liquid on the support of Example 9, in side view.

70 g of the support material KA-160 is fluidized in the fluidized bed apparatus with the help of a process gas and impregnated with the catalyst solution under the following process conditions:
a) Delivery rate: 5 ml/min
Process temperature: 80° C.
Pressure: 1.0 bar FIG. 8 shows a scanning electron microscopy image of the distribution of the ionic liquid on the support in top view. FIG. 9 shows a scanning electron microscopy image of the distribution of the ionic liquid on the support in side view.

The invention claimed is:

1. A method for producing a composite material containing a support material and an ionic liquid, the support material being present as shaped bodies having dimensions of from 1 mm to 2 cm, the method comprising the steps of fluidizing the support material in a fluidized bed or fluid bed, and applying by spray impregnation onto the fluidized support material a solution, suspension or emulsion which contains the ionic liquid, wherein the ionic liquid is a salt having a melting point below 100° C. and is present in the solution, suspension or emulsion in a range of from 1 to 10 wt.-% relative to the total weight of the solution, suspension or emulsion and wherein the spray impregnation is carried out at a temperature in the range of from 20 to 140° C.

2. The method according to claim 1, wherein the solution, suspension or emulsion contains a catalytically active component or a precursor compound thereof.

3. The method according to claim 1, wherein the support material comprises a catalytically active material.

4. The method according to claim 1, wherein the solution, suspension or emulsion contains at least one further additive.

5. The method according to claim 1, wherein the support material has dimensions of from 2 mm to 1.8 cm.

6. The method according to claim 1, wherein the support material is fluidized with the help of a process gas in the fluidized bed.

7. The method according to claim 1, wherein the spray impregnation is carried out at a pressure in the range of from 0.1 to 3 bar.

8. The method according to claim 1, wherein the ionic liquid is present in the solution, suspension or emulsion in a range of from 1.5 to 8 wt.-% relative to the total weight of the solution, suspension or emulsion.

9. The method according to claim 1, wherein the spray impregnation is carried out at a delivery rate in the range of from 0.01 to 0.2 ml solution, suspension or emulsion per minute per 1 g support material.

10. The method according to claim 1, wherein after the spray impregnation the composite material is dried at a temperature of ≥40° C.

11. The method according to claim 1, further comprising, after applying the solution, suspension or emulsion which contains the ionic liquid to the support, spraying the support with water while the support is being fluidized.

* * * * *